(12) United States Patent
Isokawa et al.

(10) Patent No.: US 9,437,037 B2
(45) Date of Patent: Sep. 6, 2016

(54) IMAGE DISPLAY DEVICE, METHOD AND PROGRAM

(71) Applicant: Hitachi Medical Corporation, Tokyo (JP)

(72) Inventors: Miho Isokawa, Tokyo (JP); Michio Oikawa, Tokyo (JP); Hiroki Taniguchi, Tokyo (JP); Hanae Yoshida, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 4 days.

(21) Appl. No.: 14/396,856

(22) PCT Filed: Apr. 12, 2013

(86) PCT No.: PCT/JP2013/061087
§ 371 (c)(1),
(2) Date: Oct. 24, 2014

(87) PCT Pub. No.: WO2013/161590
PCT Pub. Date: Oct. 31, 2013

(65) Prior Publication Data
US 2015/0109304 A1 Apr. 23, 2015

(30) Foreign Application Priority Data
Apr. 27, 2012 (JP) ................................. 2012-102842

(51) Int. Cl.
*G06T 15/00* (2011.01)
*G06T 15/08* (2011.01)
(Continued)

(52) U.S. Cl.
CPC ............... *G06T 15/08* (2013.01); *A61B 5/742* (2013.01); *A61B 6/461* (2013.01); *G06T 19/00* (2013.01);
(Continued)

(58) Field of Classification Search
CPC .. A61B 6/461; A61B 5/055; H04N 13/0456; H04N 13/0275; H04N 13/0488; G06T 15/08; G06T 2200/04; G06T 19/00; G06T 2210/41; G06T 2219/028
USPC .......................... 345/419, 427, 431, 581, 631
See application file for complete search history.

(56) References Cited

U.S. PATENT DOCUMENTS 8,248,462 B2 * 8/2012 Peterka .............. G02B 27/0093
345/19
8,463,022 B2 * 6/2013 Lipton ...................... G06T 3/00
348/441
(Continued)

FOREIGN PATENT DOCUMENTS

JP 2004-194704 A 7/2004
JP 2005-136726 A 5/2005
(Continued)

*Primary Examiner* — Phu K Nguyen
(74) *Attorney, Agent, or Firm* — Baker Botts L.L.P.

(57) ABSTRACT

In the present invention, when a 3D medical image is displayed on a 3D display, the position of accompanying information displayed at the same time is appropriately controlled. The position of the accompanying information in the coordinate system of a 3D signal value that is an item to be drawn is computed, and said position is saved in a storage unit. By integrating a 3D data area and an accompanying information area, a drawing process unit generates an output image to be displayed in a display unit, said 3D data area being drawn for an area specified by mask information that specifies an area to be drawn among an array of the 3D signal value that is the item to be drawn, and being drawn on the basis of information that specifies a drawing method for a 2D image based on the 3D signal value array, and said accompanying information area being drawn for the accompanying information, which is associated with the item to be drawn, and being drawn on the basis of position information for the accompanying information determined by a drawing control unit. The display unit displays the drawn output image.

10 Claims, 12 Drawing Sheets

(51) Int. Cl.
 *A61B 6/00* (2006.01)
 *G06T 19/00* (2011.01)
 *H04N 13/02* (2006.01)
 *A61B 5/00* (2006.01)
 *A61B 5/055* (2006.01)
 *H04N 13/04* (2006.01)

(52) U.S. Cl.
 CPC ...... *H04N 13/0275* (2013.01); *H04N 13/0488* (2013.01); *A61B 5/055* (2013.01); *G06T 2200/04* (2013.01); *G06T 2207/30004* (2013.01); *G06T 2210/41* (2013.01); *G06T 2219/028* (2013.01); *H04N 13/0456* (2013.01)

(56) References Cited

U.S. PATENT DOCUMENTS

| | | | | |
|---|---|---|---|---|
| 8,537,200 | B2* | 9/2013 | Zhang | G06T 7/0071 348/42 |
| 8,860,714 | B2* | 10/2014 | Sakuragi | G06T 7/0022 345/419 |
| 9,123,163 | B2* | 9/2015 | Hirano | G06T 15/08 |
| 2011/0235066 | A1 | 9/2011 | Sakuragi | |

FOREIGN PATENT DOCUMENTS

| | | |
|---|---|---|
| JP | 2005-303749 A | 10/2005 |
| JP | 2011-206167 A | 10/2011 |
| JP | 2012-23488 A | 2/2012 |

\* cited by examiner

FIG. 5

| 501 | 502 | 503 | 504 |
|---|---|---|---|
| TYPE OF ACCOMPANYING INFORMATION | FORMAT OF ACCOMPANYING INFORMATION | INTRA-SCREEN POSITION | POSITIONAL RELEVANCE TO 3D DATA COORDINATES |
| PATIENT - INSPECTION INFORMATION | 2D (CHARACTER) | FIXED | NOT PRESENT |
| DISPLAY PARAMETER INFORMATION | 2D (CHARACTER) | FIXED | NOT PRESENT |
| COLOR SCALE | 2D (DRAWING) | FIXED | NOT PRESENT |
| SIZE SCALE | 2D (SCALE) | FIXED | NOT PRESENT |
| MOUSE CURSOR | 2D/3D (DRAWING) | CAN BE SHIFTED BY USER OPERATION | NOT PRESENT |
| POSTURE INFORMATION | 3D (DRAWING + CHARACTER) | FIXED | NOT PRESENT |
| MEASUREMENT TOOL | 3D (DRAWING + SCALE) | CAN BE SHIFTED BY USER OPERATION | PRESENT |
| MARKER | POINT (DRAWING) | SHIFTED IN RELATION TO 3D DATA | PRESENT |
| ROI | 2D/3D (DRAWING) | SHIFTED IN RELATION TO 3D DATA | PRESENT |
| LEAD LINE | 3D (DRAWING) | SHIFTED IN RELATION TO 3D DATA - ACCOMPANYING INFORMATION | PRESENT |
| COMMENT | 2D (CHARACTER) | OPTIONAL | INDIRECTLY PRESENT |

IMAGE DISPLAY DEVICE, METHOD AND PROGRAM

TECHNICAL FIELD

The present invention relates to an image display device, and more particularly relates to an image display technology when drawing a 3D medical image by using 3D data collected by a medical imaging device such as an MRI (Magnetic Resonance Imaging) device (a nuclear magnetic resonance image diagnostic device), a CT (Computed Tomography) device (a computed non-invasive imaging device) and so forth.

BACKGROUND ART

Recently, it has become possible to collect massive section patterns (section images) in association with high functionality of the medical image imaging device such as the MRI device, the CT device and so forth. In addition, it has become possible to perform generation of 3D data from the section patterns, drawing of a medical image from the 3D data, and image processing on the medical image at a high speed and with high accuracy in association with high functionality of a medical image display device.

When radiographic image interpretation (a diagnosis based on the medical image) using the medical image is to be performed, it is also possible to stereoscopically view a 3D medical image that has been generated from the 3D data by displaying on a volumetric display in order to use morphological knowledge. At that time, there are cases when accompanying information such as annotations such as an ROI (Region of Interest: a space of interest), impressions and so forth, a mouse cursor, a measurement tool, various kinds of character information and so forth that are not included in the section patterns collected from the medical image imaging device is displayed in superimposition on the 3D medical image. It is feared that a stereoscopic effect of the 3D medical image may be lost and visibility of the accompanying information may be reduced unless arrangement of the accompanying information is appropriately performed at that time.

With regard to arrangement of the accompanying information when the 3D medical image is to be stereoscopically displayed, Patent Literature 1 is adapted to superimpose the annotation on the 3D image to display them stereoscopically by specifying a position on a coordinate system of the 3D image with regard to an arrow-shaped annotation that has been added in a 2D section pattern and adding it to a corresponding position on a parallax image for each eye for performing stereoscopic display.

In addition, in Patent Literature 2, a stereoscopically viewing method that the stereoscopic scale is superimposed on a stereoscopic image by displaying scales for the left eye and the right eye according to scale values in the stereoscopic image by including them respectively in the parallax images for the left eye and the right eye is proposed.

CITATION LIST

Patent Literature

PTL 1: Japanese Patent Application Laid-Open No. 2011-206167
PTL 2: Japanese Patent Application Laid-Open No. 2005-136726

SUMMARY OF INVENTION

Technical Problem

In a case where the accompanying information is to be displayed on the volumetric display by superimposing it on the 3D medial image, it is necessary to appropriately adjust a depth that the accompanying information is to be arranged to within a range that readability and resolution are not reduced and visual fatigue is not increased in accordance with an implementation system of the volumetric display.

In addition, when the 3D position of the accompanying information is fixed, there are cases when the visibility is reduced in accordance with a viewpoint position and an amount of information to be displayed on the screen, and therefore it is necessary to take a display position in the screen into account when controlling arrangement.

That is, in prior art, there is such a problem that the medical image and the accompanying information based on the 3D data cannot be appropriately displayed on the volumetric display.

Solution to Problem

In order to solve the aforementioned problem, an image display device according to the present invention is provided with the following configurations.

That is, it has a display unit that displays an output image that has been drawn, a storage unit that has stored an array of 3D signal values that is a drawing object, mask information for designating an object area for drawing in the array of the 3D signal values, information for designating a drawing method for a 2D image based on the array of the 3D signal values, accompanying information that has been related to the drawing object, information on arrangement and display plans that has been set for the accompanying information, and information relevant to characteristics of the display unit, a drawing control unit that computes the position of the accompanying information in a coordinate system of the 3D signal value that is to be the drawing object on the basis of the mask information, the information for designating the drawing method for the 2D image, the information on the arrangement and display plans and the information relevant to the characteristics of the display unit and stores it into the storage unit and a drawing processing unit that generates an output image to be displayed on the display unit by integrating together a 3D data area to be drawn on the basis of the information for designating the drawing method for the 2D image for an area that has been designated by the mask information in the array of 3D signal values that is the drawing object and an accompanying information area to be drawn on the basis of information on the position of the accompanying information that has been determined by the drawing control unit for the accompanying information.

Advantageous Effects of Invention

According to the present invention, the medical image and the accompanying information based on the 3D data can be appropriately displayed on the volumetric display.

BRIEF DESCRIPTION OF DRAWINGS

FIG. 5 is a diagram showing an example of handling of display/arrangement of accompanying information according to an embodiment of the present invention.

DESCRIPTION OF EMBODIMENTS

In the following, modes for embodying a medical image imaging device and a medical information management server according to the present invention will be described with reference to the appended drawings.

Figure 1:
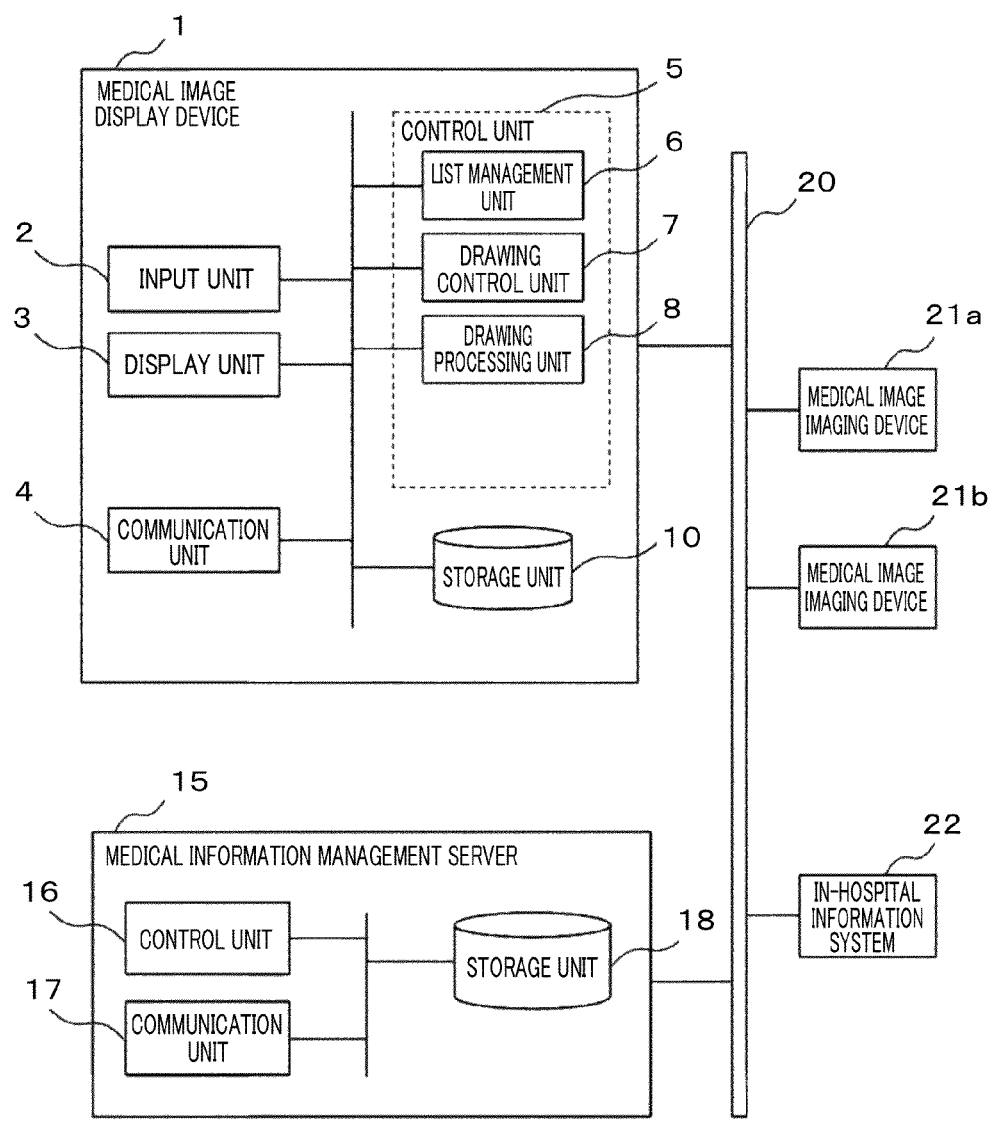
FIG. 1 is a block diagram showing an outline of configurations of a medical image display device and a medical information management server according to an embodiment of the present invention.

First, configurations of the medical image imaging device and the medical information management server according to the present embodiment will be described with reference to FIG. 1.

A medical image imaging device 21 such as the MRI device, the CT device or the like collects section patterns (images that are configured by signal values on a section) by imaging and transmits them to a medical information management server 15 over a network 20. Incidentally, this network 20 may be, for example, an intranet in a hospital, an inspection agency and so forth and may be the Internet.

A medical image display device 1 is a computer device that is connected to the medical information management server 15 to display the section pattern that the medial image imaging device 21 has imaged, or a medical image that has been generated by drawing 3D data constructed from the section pattern such that a user performs radiographic image interpretation and inputting of diagnosis information, and is configured by, for example, a CPU (Central Processing Unit), a memory, a ROM (Read Only memory), an HDD (Hard Disk Drive), an input/output interface, an LCD (Liquid Crystal Display), a keyboard, a mouse and so forth.

The medical image display device 1 is provided with an input unit 2 that processes an input from the user, a display unit 3 that holds a screen for displaying the medical image, a communication unit 4 that performs transmission and reception of information with the medical information management server 15 and an in-hospital information system 22, a list management unit 6 that manages lists of radiographic image interpretation request matters and medical information, a user list and so forth, a drawing control unit 7 that performs management of a drawing object and control of the position thereof, a drawing processing unit 8 that performs conversion processing and drawing of the section pattern and the 3D data, and a storage unit 10 that temporarily saves the medical images, drawing settings, diagnosis information and so forth. In the example in FIG. 1, the list management unit 6, the drawing control unit 7 and the drawing processing unit 8 are parts of a control unit 5. The control unit 5 is implemented, for example, by executing a program stored in the memory by the CPU. Therefore, processing that the control unit 5 (that is, the list management unit 6, the drawing control unit 7 and the drawing processing unit 8) executes in the following description is executed by the CPU that follows the program stored in the memory in reality.

Incidentally, the medial image display device 1 may also be a device that mainly aims to browse the medical images and the diagnosis information without performing radiographic image interpretation.

The medical information management server 15 is a so-called PACS (Picture Archiving and Communication System: a medical image diagnosis support system), is adapted to manage medical information such as the medical images, the diagnosis information, information relevant to patients and so forth and consists of a control unit 16, a communication unit 17 and a storage unit 18.

The control unit 16 performs storage processing of storing data that the communication unit 17 has received into a database that the storage unit 18 possesses, search processing of acquiring data according to a request for data from the medical image display device 1 from the database that the storage unit 18 possesses and so forth. The control unit 16 is implemented by, for example, the CPU and the memory.

The communication unit 17 performs transmission and reception of data with the medical image display device 1, the medical image imaging device 21, the in-hospital information system 22 that manages information on patients, inspections, accounts and so forth and so forth.

The storage unit 18 is provided with the database that accumulates information on the section patterns collected from the medical image imaging device 21, the medical images generated by the medical image display device 1, the drawing settings, the diagnosis information, reports and so forth, information relevant to the patients acquired from the in-hospital information system 22 and so forth. The storage unit 18 is implemented by, for example, the HDD and so forth. Incidentally, the medical information management server 5 that has the storage unit 18 provided with the database for all pieces of the aforementioned information may be used, a plurality of the medical information management servers 15 that have the storage units 18 provided with only specific databases may be cooperatively used, and the in-hospital information system 22 that holds a database that is equivalent thereto may be used in cooperation therewith.

Next, a configuration example of information relevant to drawing of the medical image will be described by using FIG. 2.

Figure 2:
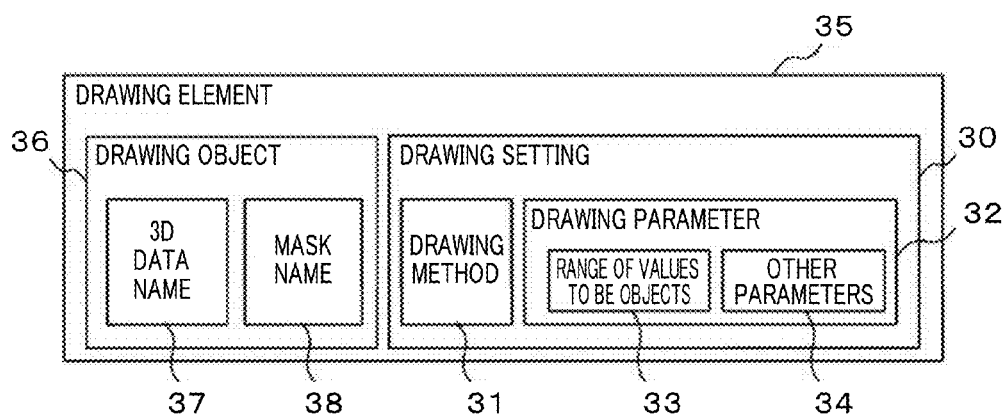
FIG. 2 is a diagram showing a data structure of a drawing element according to an embodiment of the present invention.

Drawing setting 30 shown in FIG. 2 is information consisting of a drawing method 31 and a drawing parameter 32.

The drawing method 31 is information for identifying a method of performing projection processing on the 3D data. Speaking in more detail, the projection processing on the 3D data is processing of projecting an image onto a 2D screen on the basis of a 3D array of signal values (for example, CT values) constructed from the section patterns acquired by the medial image imaging device 21. As a method of performing such projection processing, for example, there is VR (Volume Rendering), SR (Surface Rendering), MIP (Maximum Intensity Projection: a maximum value projection method), MinIP (Minimum Intensity Projection: a minimum value projection method), VE (Virtual Endoscopy: a virtual endoscopic image) or the like. In the following, a drawing method of performing projection processing on the 3D data will be described in the present embodiment.

The drawing parameter 32 is a parameter to be applied in order to generate 2D data by the above-mentioned drawing method and to display an image on the basis of that 2D data. Specifically, the drawing parameter 32 is configured by a range of values to be objects 33 and other parameters 34 relevant to the drawing method 31.

The range of values to be objects 33 is adapted to limit the range of signal values to be application objects for the other parameters 34 relative to the range of signal values measured by the medical image imaging device 21. For example, the range of CT values (signal values measured by the CT device) is generally about −2000 to +4000, and the range of signal values of about 60 to 90 is designated as the range of values to be objects 33 when the drawing parameter 32 for the brain is to be set. The other parameters 34 are not applied to out-of-range signal values.

The other parameters 34 include a window level, a window width, an opacity curve (allocation of opacity and color to the signal value), information on a light source, a viewpoint position in 3D space and so forth, for example, in a case where the drawing method 31 is VR.

The drawing setting 30 is information not depending on specific 3D data. That is, it is possible to reuse the drawing setting that has been utilized for drawing of certain 3D data when similar drawing is to be performed on optional 3D data other than that. A plurality of the drawing settings 30 consisting of combinations of the various drawing methods 31 with the various drawing parameters 32 may be stored in the storage unit 18 and so forth.

The drawing element 35 is a combination of a drawing object 36 with the drawing setting 30. The drawing object 36 is information for designating an object (that is, an object for drawing on the basis of the drawing setting 30) to which the drawing setting 30 is to be applied and is configured by a 3D data name 37 and a mask name 38.

The 3D data name 37 is information for identifying the 3D data (that is, the array of 3D signal values) and the 3D data of the object to which the drawing setting 30 is to be applied is designated by this.

The mask is information for designating a drawing object area in the 3D space that the 3D data belongs and includes binary data indicating whether each voxel (a coordinate grid point in the 3D space) of the 3D data is an object for drawing. Although the 3D data and the mask are large in information amount and therefore the drawing object 36 of the present embodiment includes only the names (that is, the 3D data name 37 and the mask name 38) that serve as keys for calling the respective ones, the drawing object 36 may include data itself.

The drawing element 35 is information relevant to specific 3D data and therefore it is used in order to perform reproduction of drawing relevant to the specific 3D data, not being reused to other 3D data. It is also possible to configure the drawing element 35 by allocating the drawing object 36 to the drawing setting 30.

The drawing control unit 7 manages the drawing setting 30 or the drawing element 35, and the drawing processing unit 8 performs drawing processing by using the drawing element 35. It is possible for the drawing control unit 7 to save the drawing setting 30 or the drawing element 35 in the storage unit 10 of the medical image display device 1 or the storage unit 18 of the medical information management server 15 so as to call it as required to use it as it is or to use it by making a change thereto.

In addition, it is also possible to handle the drawing setting 30 or the drawing element 35 as a set that a plurality of respective ones have been combined together in order to generate a compound medical image.

The compound medical image is an image that drawing has been performed in a state that the plurality of drawing settings 30 or drawing objects 36 are mixed, and it is possible to improve understandability of the medical image and accuracy in radiographic image interpretation thereof by using the drawing setting that is different for every 3D data or specific area.

Figure 4A:
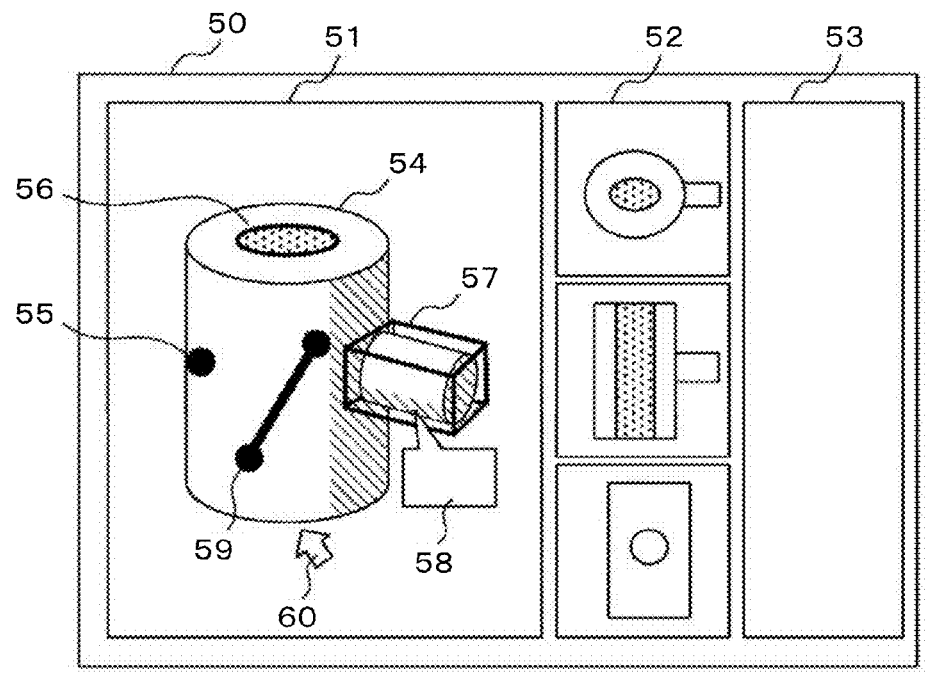
FIG. 4A is a diagram showing an example of a screen that the display unit according to an embodiment of the present invention displays.
Figure 4B:
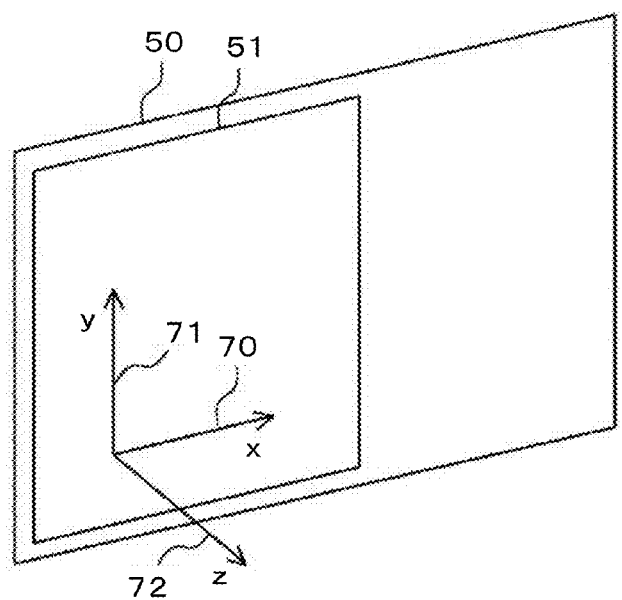
FIG. 4B is a diagram showing the screen and definition of a coordinate system according to an embodiment of the present invention.

Here, an area of the voxel (the point on the 3D unit grid) that is included in a mask area designated by the mask name 38 in a 3D coordinate space that the 3D data on a radiographic image interpretation object has been defined and to which the opacity that is larger than 0 and the color are allocated by the drawing method 31 and the drawing parameter 32 to be set as an object for drawing processing will be referred to as a valid 3D data area 91. For example, a display object 54 in FIG. 4A is the one that the valid 3D data area 91 has been drawn.

Next, characteristics of the display unit 3 and a configuration example of information on display unit 40 to be saved in the storage unit 10 will be described. Here, a display that stereoscopic display is possible is used as the display unit 3. In an implementation system for stereoscopic display, there are various systems such as a wavelength division system such as anaglyph, spectroscopy and so forth, a time division system such as shutter glasses and so forth, a space division system such as deflection, barrier, lenticular and so forth, a light beam reproduction system such as Integral Photography, hologram, superimposed projection and so forth and so forth. Characteristics such as a range of projecting amount that makes it possible to appropriately perform stereoscopic vision, a change in image quality (easiness of recognition of the image) in accordance with the depth position and so forth are different depending on the selected system. When it is displayed beyond the proper range of projecting amount, it is feared that the user may suffer from the visual fatigue and readability may be reduced.

In addition, since the format, the amount and generation conditions of output images to be displayed on the display unit 3 are different depending on the system for stereoscopic display, it is necessary for the control unit 5 to use the information on display unit 40 when generating the output image. The information on display unit 40 may be saved in the storage unit 10 and may be set when the display unit 3 is to be connected, and a plurality of pieces of information relevant to several systems may be accumulated in the storage unit 10 in advance and may be changed over as required.

Further, it is also possible to use a display that cannot perform stereoscopic display as the display unit 3 and, at that time, it is also possible to include information that stereoscopic display is impossible as the information on display unit 40 and to display the output image that has been drawn in accordance with a drawing procedure that will be described in the present embodiment, without stereoscopically displaying it.

Figure 3:
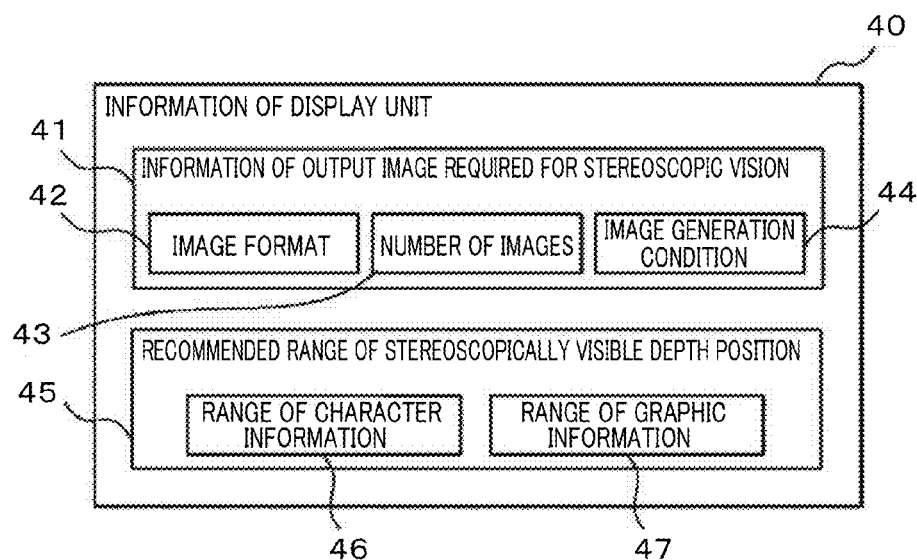
FIG. 3 is a diagram showing a data structure of information of a display unit according to an embodiment of the present invention.

FIG. 3 is an example of the information on display unit 40 that makes stereoscopic display possible to be saved in the storage unit 10. The information on display unit 40 includes information on output image required for stereoscopic vision 41 such as an image format 42, a number of images 43, an image generation condition 44 and so forth, and a recommended range of appropriately stereoscopically visible depth values 45 for each of character information and graphic information. Further, in a case where the image quality (easiness of recognition of the image) on an x-y plane that is parallel with a screen 50 is changed in accordance with the depth value on a z-axis 72 that is vertical to the screen 50 of the display unit 3, information thereof may be included. When arrangement is to be determined in regard to the drawing object whose arrangement is variable, the drawing control unit 7 refers to the information on display unit 40 saved in the storage unit 10, performs arrangement within the recommended range of stereoscopically visible depth values 45 and performs drawing of an image of the format designated by the image format 42 by the amount designated by the number of images 43 and in accordance with the image generation condition 44.

Next, an example of the screen 50 of the display unit 3 and the accompanying information will be described by using FIG. 4A. The whole of the screen 50 to be displayed on the display unit 3 may be stereoscopically displayed or only one part in the screen may be stereoscopically displayed. FIG. 4A is the example that a stereoscopic image display area 51 is partially provided, and a section pattern display area 52, a tool area 53 for displaying various operation menus, libraries, setting contents and so forth and so forth are included in addition to the stereoscopic image display area 51. In the stereoscopic image display area 51, the medical image (that is, the display object) 54 that has been drawn on the basis of the drawing element 35 is to be stereoscopically displayed. Here, all pieces of information other than the medical image 54 generated from the drawing element 35 to be displayed in the stereoscopic image display area 51 will be referred to as the accompanying information. As examples of the accompanying information, there are a mouse cursor 60 by which the user performs an inputting operation, character information relevant to the patients, the inspections and the drawing settings, a color scale for indicating allocation of the color to the value of the 3D data, a size scale for indicating the size of the medical image, a marker 55 and ROIs 56, 57 allocated to specific positions on the medical image, a measurement tool 59 for measuring a distance between two points, a peripheral length, an area, a volume and so forth, a comment 58 such as a diagnostic impression and so forth, posture information for indicating a direction that he is looking and so forth. These pieces of accompanying information are generated from the information included in the drawing element 35, the information that the user has given and has been accumulated in the storage unit 10 and so forth.

When displaying the accompanying information in the stereoscopic image display area 51, it is necessary to perform drawing by setting the depth position. However, a projecting method of generating the medical image 54 from the 3D data is, in many cases, a specific method used for radiographic image interpretation such as VR (Volume Rendering) and so forth, and it is necessary to draw the accompanying information by another method such as polygon rendering and so forth. Thus, as in Japanese Patent Application Laid-Open No. 2004-86428, a method of separately generating the output images and depth images (the one that the value of the z-axis 72 of the voxel located on the front-most side in the valid 3D data area 91 has been recorded on a projected light beam that a pixel value thereof is to be computed in regard to each pixel in the output image) respectively for the 3D data and the accompanying information and superposing them while referring to the depth image is proposed. It is supposed that also in the present image display device 1, the drawing processing unit 8 performs integrated processing of the output images by using the depth image. However, as the method of generating the output image by superimposing the accompanying information on the 3D data, a method other than this may be used.

Handling of the position for displaying the accompanying drawing is different depending on the property of the accompanying information. The property of the accompanying information consists of an accompanying information type 501, a (display) format of accompanying information 502, an intra-screen position 503 and positional relevance to 3D data coordinates 504.

An example of handling of the display position according to the property of accompanying information is shown in FIG. 5. Since, for example, the character information relevant to the patients and inspections, and the drawing setting, the color scale, the size scale, the posture information and so forth are information not depending on the display position of the medical image 54, it is thought that fixing them to specific positions in the stereoscopic image display area 51 makes it easier to see them. However, the one to be fixed here is a position in the x-y plane that an x-axis 70 and a y-axis 71 that are parallel with the screen 50 have been defined and there are cases when the position on the z-axis 72 corresponding to the depth may be changed. In addition, ON/OFF of display may be switched as required.

Figure 6:
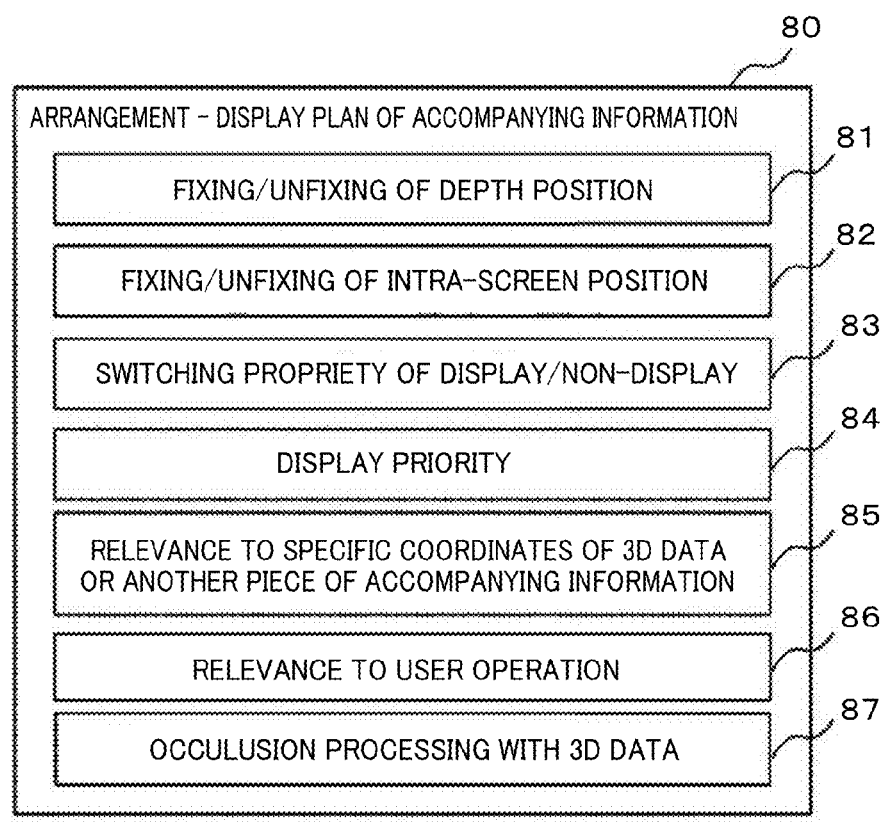
FIG. 6 is a diagram showing display/arrangement plans of the accompanying information according to an embodiment of the present invention.

Arrangement/display plan of accompanying information 80 such as an example shown in FIG. 5 is allocated to each piece of the accompanying information and is saved in the storage unit together with the accompanying information. A configuration example of the arrangement/display plan of accompanying information 80 is shown in FIG. 6. A system manager and others may set this information in advance and the user may change the settings thereof individually. In addition, they may be allocated in a lump for every type of the accompanying information and the setting may be changed for every piece of the accompanying information.

The arrangement/display plan of accompanying information 80 consists of fixing/unfixing of depth position 81, fixing/unfixing of intra-screen position 82, switching propriety of display/non-display 83, display priority 84, relevance to specific coordinate position of 3D data or another piece of accompanying information 85, relevance to user operation 86 and occulusion processing with 3D data 87. The items 81 to 84 and 86 in FIG. 6 correspond to the intra-screen position 503 in FIG. 5 and the item 85 corresponds to the positional relevance to 3D data coordinates 504 in FIG. 5.

The fixing/unfixing of depth position 81 is adapted to set whether the position on the z-axis that is vertical to the screen of the display unit is to be fixed. The fixing/unfixing of intra-screen position 82 is adapted to set whether the position on the x-y plane that is parallel with the screen 50 of the display unit 3 is to be fixed. In a case where they are to be fixed respectively, coordinate values to be recommended are also saved in the storage unit 10. The display priority 84 includes information relevant to a display method according to the priority such that it is always displayed, it is displayed in a displayable area, if any, preferential display is performed in accordance with the priority in a case where there exist a plurality of pieces of accompanying information of the same type and so forth, and the plurality of display methods may be combined with one another instead of selecting any one of them.

As for the relevance to specific coordinate position of 3D data or another piece of accompanying information 85, there exist a case of displaying it in superimposition on the specific coordinate position of the 3D data as in the case of, for example, the ROI and so forth, a case of displaying it in the vicinity by drawing a lead line or the like for the specific coordinate position of the 3D data or another piece of accompanying information as in the case of the comment and so forth and so forth. The relevance to user operation 86 means that the relevance is present when there exists the one such as, for example, the mouse cursor 60 that the position is determined in accordance with mouse input of the user.

The occulusion processing with 3D data 87 is adapted to, in a case where when arrangement has been appropriately performed on the accompanying information within the recommended range of the stereoscopically displaceable depth, overlapping or occulusion (a state that an object located on an inner part disappears obstructed by an object located on the front) with the 3D data occurs and the 3D data is displayed on the front side ahead of the accompanying information, set whether it is to be displayed as it is (the stereoscopic effect is preferred) in order not to lose the stereoscopic effect of the 3D data although the visibility of the accompanying information is obstructed, or to set whether the accompanying information is to be preferentially displayed (information display is preferred) in order to prefer the visibility of the accompanying information although the stereoscopic effect of volume data is lost. Incidentally, also in a case where it has been set that the stereoscopic effect is preferred, the accompanying information may be temporarily displayed preferentially by operations such as mouse click, mouse over and so forth by the user.

Figure 7:
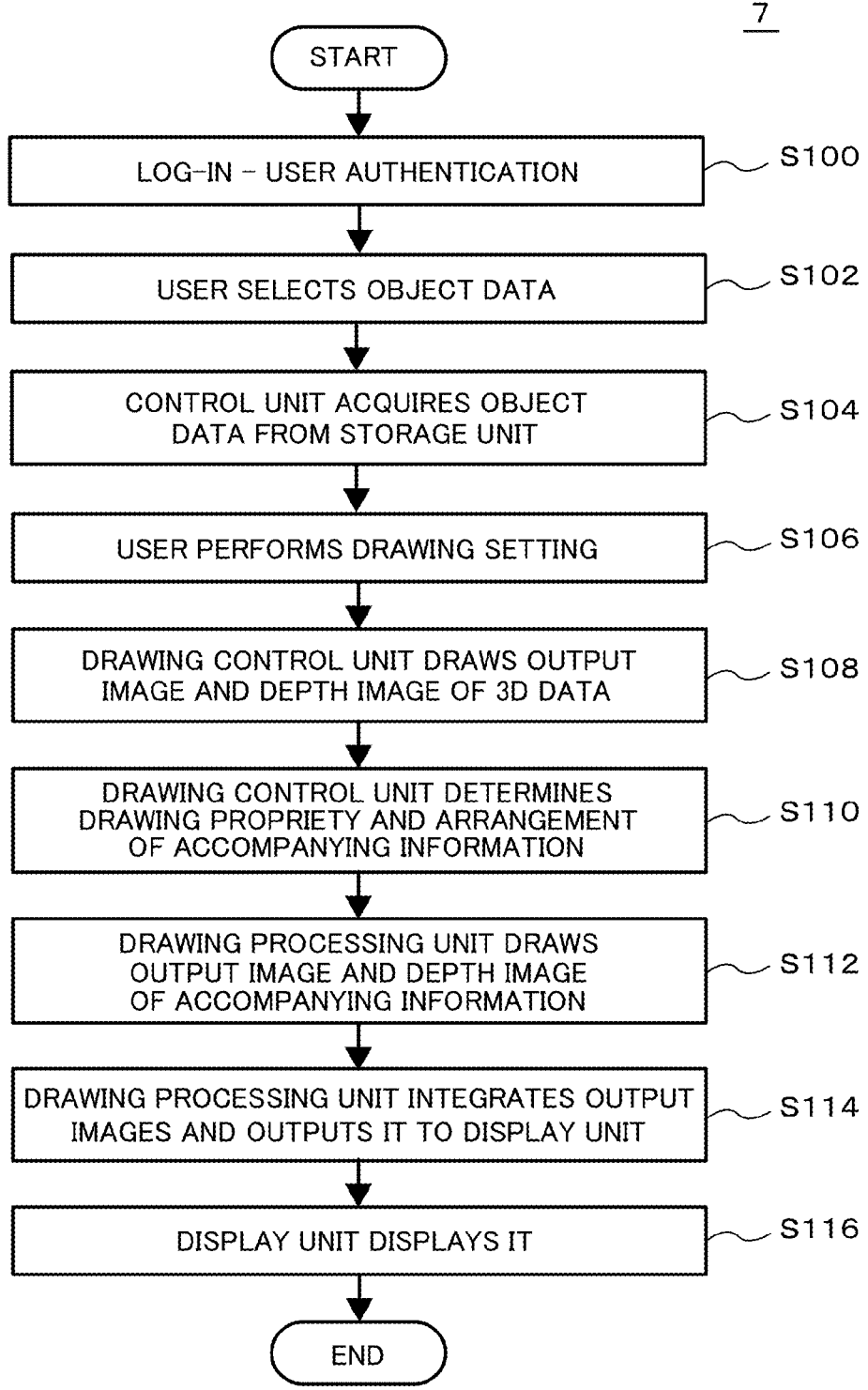
FIG. 7 is a flowchart showing display processing of a medical image that includes the accompanying information according to an embodiment of the present invention.

Next, an example of a flow that the user performs display of the medical image including the accompanying information by using the medical image display device 1 according to the present embodiment and accompanying information positioning processing that the drawing control unit 7 performs will be described using FIG. 7. Here, as the user, a radiologist in the department of radiology who has accepted a request for radiographic image interpretation and others are supposed.

When the input unit 2 of the medical image display device 1 accepts log-in processing from the user, the list management unit 6 performs user authentication processing on the basis of the user list (S100). The list management unit 6 generates the list of radiographic image interpretation request matters and the user selects information on a radiographic image interpretation object (S102). Here, as the information on the radiographic image interpretation object, a set of section patterns collected by the medical image imaging device 21, the 3D data that has been configured in advance by using the set of section patterns, the medical image that drawing has been performed on the 3D data and so forth are supposed. In addition, the user searches for information that the medical information management server 15 accumulates by using the patient name, the inspection name, the image set name and so forth as keys, thereby it is also possible to select the information on the radiographic image interpretation object.

The communication unit 4 transmits a request for data to the medical information management server 15 in accordance with selection of the user. The medical information management server 15 searches for and acquires the requested information (that is, the information on the radiographic image interpretation object that has been selected by the user) from the storage unit 18 and transmits information that matches it from the communication unit 17 to the medical image display device 1. When the communication unit 4 of the medical image display device 1 accepts the information on the radiographic image interpretation object, in a case where the information concerned has been the set of section patterns, the drawing processing unit 8 configures the 3D data from the set of section patterns and accumulates it in the storage unit 10 (S104). At that time, in a case where there exists accompanying information such as the ROI, the diagnostic impressions and so forth that have been related to the radiographic image interpretation object, it acquires them from the medical information management server 15 simultaneously and accumulates them in the storage unit 10.

Next, the user sets the drawing element 35 consisting of the combination of the drawing method 31, the drawing parameter 32, the 3D data name 37 of the radiographic image interpretation object and the mask name 38 shown in FIG. 2 by using the tool area 53 of the screen 50 that the display unit 3 possesses (S106). The drawing processing unit 8 performs drawing of the output image and the depth image of the 3D data on the basis of this drawing element 35 and the information on output image required for stereoscopic vision 41 and saves them in the storage unit 10 (S108). In a case where the information on output image required for stereoscopic vision 41 indicates, for example, two left and right eye images, projection processing is performed from viewpoint positions for the right eye and the left eye and two output images and depth images are drawn for each of them.

In addition, in the course of this drawing, the drawing processing unit 8 also performs computation of the valid 3D data area 91 and accumulates it in the storage unit 10. Here, in a case where the front side on the z-axis 72 of the valid 3D data area 91 is beyond the recommended range of stereoscopically visible depth value 45 of the display unit 3, the drawing control unit 7 may shift the position on the z-axis 72 toward the inner side of the screen 50. In addition, it is also possible for the user to avoid this state by performing a shifting operation of the viewpoint position included in the drawing setting 30 or the display position of the 3D data.

Next, the drawing control unit 7 acquires the valid 3D data area 91, the accompanying information that has been related to the 3D data and the arrangement/display plan of each piece of accompanying information 80 from the storage unit 10 and determines the propriety of drawing of each piece of accompanying information and the position thereof in the 3D space (S110). At that time, in a case where the arrangement/display plan of each piece of accompanying information 80 has been acquired together with the accompanying drawing from the medical information management server 15, it is used, while in a case where it has not been given to the accompanying information, initial setting that has been allocated for every accompanying information type 501 accumulated in the storage unit 10 is used. A procedure of position determination will be described in detail later.

The drawing processing unit 8 performs drawing of the output image and the depth image of the accompanying information on the basis of the position of the accompanying information that this drawing control unit 7 has determined and the information on output image required for stereoscopic vision 41 and saves them in the storage unit 10 (S112). In addition, in a case where there exists accompanying information that the occulusion processing with 3D data 87 is set to be preferred in information display in setting of the arrangement—display plan of accompanying information 80, preferential display information (bit information) that indicates with two values whether each pixel is an area that display of the accompanying information is preferred is also generated. The preferential display information is held corresponding to data of each pixel.

Next, the drawing processing unit 8 performs such integrated processing that the one (the one to be displayed on the front) that is larger in value (z) of a depth image in regard to each pixel is set as a display object and the pixel value of the output image thereof is copied as the pixel value of the output image to be output to the display unit 3, while referring to the 3D data and the depth image of the accompanying information (S114). At that time, in a case where there exists the previously described preferential display information, it is supposed to use the pixel of the output image of the accompanying information not depending on the depth image in regard to the pixel that has been so set that the accompanying information is to be preferentially displayed.

The drawing processing unit 8 outputs an integrated output image to the display unit 3 and the display unit 3 displays it in the stereoscopic image display area 51 in the screen 50 (S116).

In a case where the user has performed operations such as setting change, addition of accompanying information and so forth on this displayed stereoscopic image, processes in step S108 or S110 and the subsequent ones are performed again as required.

Figure 8:
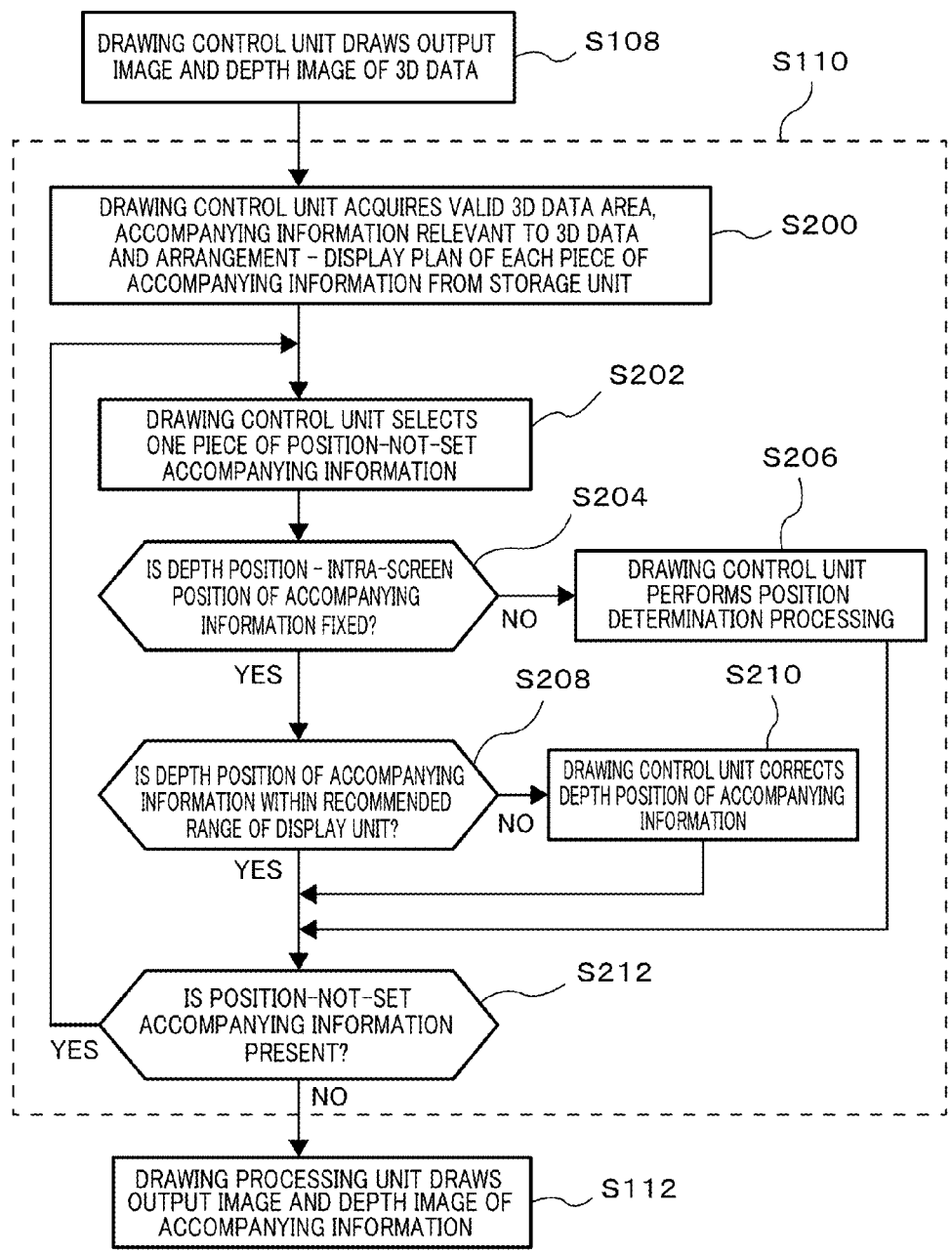
FIG. 8 is a flowchart showing an outline of position determination processing for accompanying information according to an embodiment of the present invention.

Next, position determination processing for accompanying information (S110) will be described by using FIG. 8. First, the drawing control unit 7 acquires the valid 3D data area 91 generated by the drawing processing unit 8, the accompanying information relevant to the 3D data and the arrangement/display plan of each piece of accompanying information 80 from the storage unit 10 (S200). Next, it selects one from a group of pieces of the accompanying information (S202) and checks to see whether the depth position or the intra-screen position is fixed (S204). When any one of them is unfixed, the drawing control unit 7 performs position determination processing (S206). Details of this processing will be further described later.

Next, in a case where the depth position is fixed and a recommended value is set in step S202, the drawing control unit 7 checks to see whether it is included in the recommended range of stereoscopically displaceable depth 45 of the display unit 3 (S208), and in a case where it is out of range, it corrects the depth position of the accompanying information to within the recommended range of stereoscopically displaceable depth 45 (S210).

In a case where there exists accompanying information whose position is not yet set (S212), processes in steps S202 to S210 are repeated and after arrangement of all of them has been terminated, the drawing processing unit 8 performs drawing (S112).

Figure 9:
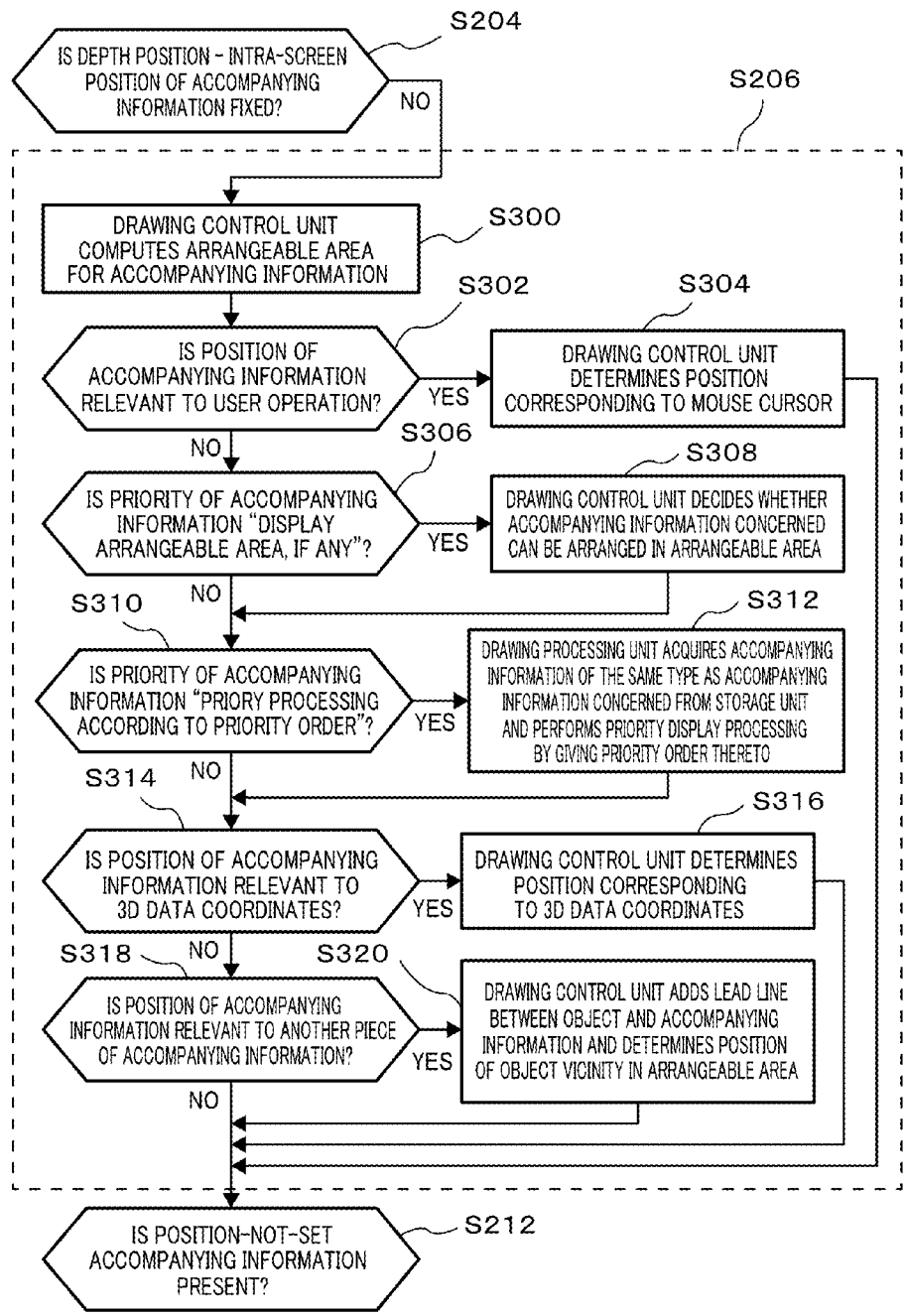
FIG. 9 is a flowchart showing processing of position determination processing for accompanying information that a depth position or an intra-screen position is unfixed according to an embodiment of the present invention.
Figure 10A:
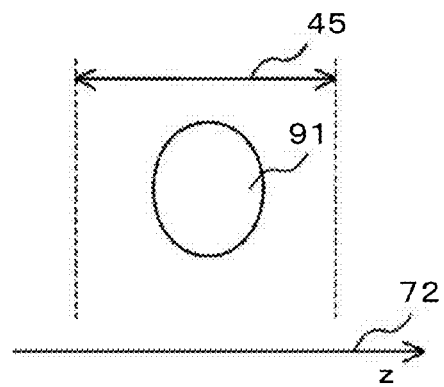
FIG. 10A is a diagram showing a positional relation between a recommended range of a stereoscopically visible depth and a valid 3D data area according to an embodiment of the present invention.
Figure 10B:
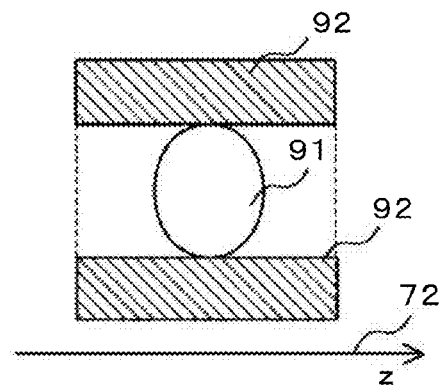
FIG. 10B is a diagram showing an area that occulusion with the valid 3D data does not occur according to an embodiment of the present invention.
Figure 10C:
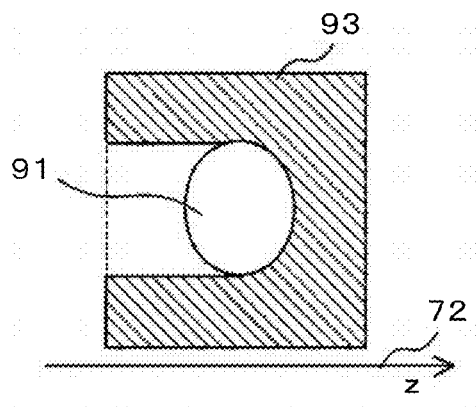
FIG. 10C is a diagram showing an area that does not overlap the valid 3D data area and does not become a back face of the valid 3D data area by occulusion according to an embodiment of the present invention.

The position determination processing for the accompanying information that the depth position or the intra-screen position is unfixed (S206) will be described in detail by using FIG. 9 to FIG. 11. First, the drawing control unit 7 saves any one of an area 92 that occulusion with the valid 3D data area 91 does not occur as shown in FIG. 10B, or an area 93 that does not overlap the valid 3D data area 91 and does not come behind the valid 3D data area 91 as shown in FIG. 10C in the storage unit 10 as an arrangeable area (S300) in regard to the 3D area that the value of the z-axis 72 is within the recommended range of stereoscopically visible depth 54 as shown in FIG. 10A. Which one of them is to be used may be selected automatically or by user setting by taking the amount of the accompanying information to be arranged, the size of the stereoscopic image display area 51 and so forth into account.

Next, the drawing control unit 7 refers to the arrangement/display plan of accompanying information 80, and in a case where it is relevant to the user operation, arranges the accompanying information on the position according to the mouse input (S304). At that time, the one that has been determined by the mouse input is 2D coordinates in the x-y plane, and the depth position on the z-axis 72 may be set by using another means and may be set to a position that the image quality (easiness of image recognition) is the most improved within the recommended range of stereoscopically visible depth 45, and the projecting amount may be set to 0 (that is, z=0).

In setting of the display priority of accompanying information 84, in a case where "Display It In Arrangeable Area, If Any" is set (S306), a decision as to whether this accompanying information can be arranged in the arrangeable area, that is, whether there exists a space that this accompanying information can be arranged in the arrangeable area is made (S308). In addition, in setting of the display priority 84, in a case where "Perform Priority Processing according to Priority Order" is set (S310), the drawing control unit 7 acquires all pieces of the accompanying information of the same type in the accompanying information to be displayed from the storage unit 10, performs prioritization using the importance of the accompanying information, the similarity in drawing setting 30 when the user has given the accompanying information and so forth as standards and sets the display method such that accompanying information that is higher in priority order is more increased in visibility (S312).

Examples of the display method that the visibility is increased in accordance with the priority are shown in FIGS.

Figure 11A:
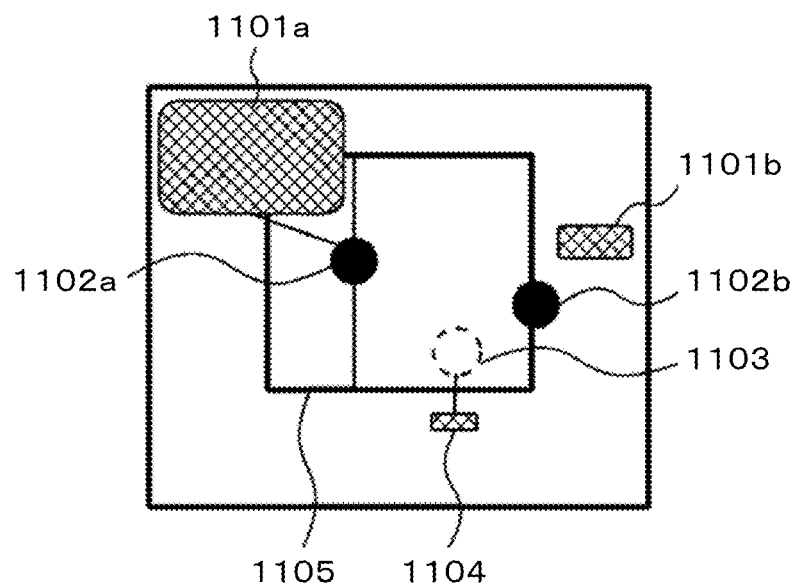
FIG. 11A is a diagram that the size has been changed as preferential display processing of the accompanying information according to an embodiment of the present invention.
Figure 11B:
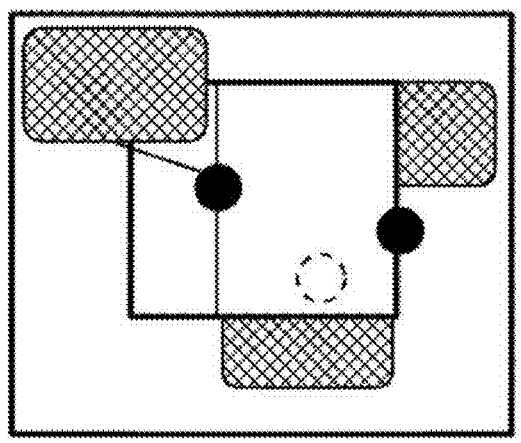
FIG. 11B is a diagram that the depth position has been changed as the preferential display processing of the accompanying information according to an embodiment of the present invention.
Figure 11C:
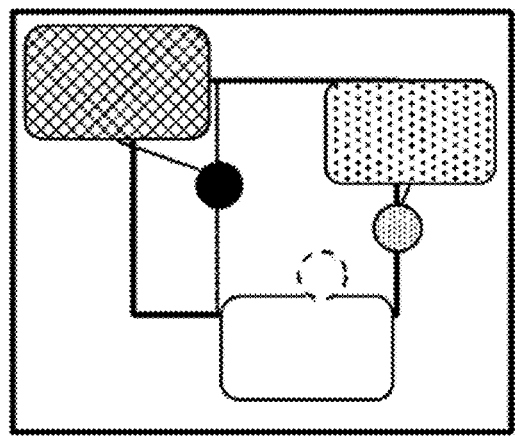
FIG. 11C is a diagram that the color or transparency has been changed as the preferential display processing of the accompanying information according to an embodiment of the present invention.
Figure 11D:
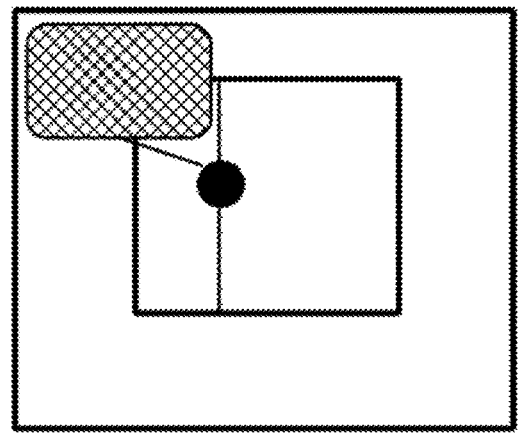
FIG. 11D is a diagram that only things that are high in priority order have been displayed as the preferential display processing of the accompanying information according to an embodiment of the present invention.
Figure 12:
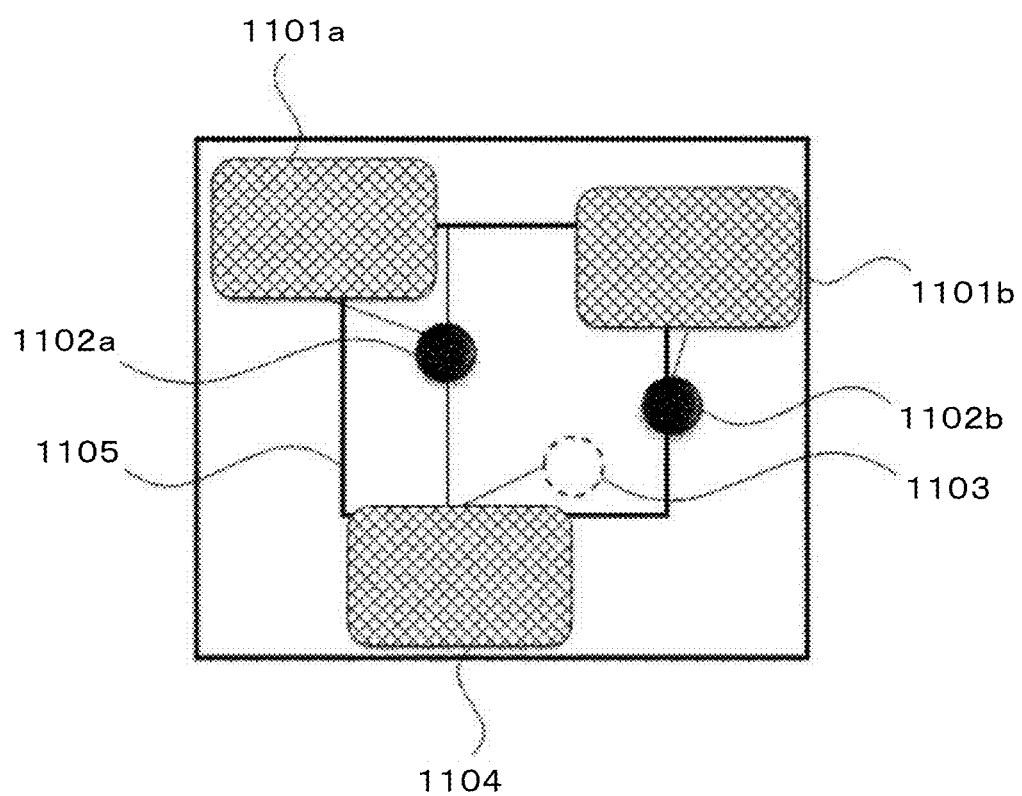
FIG. 12 is a diagram showing an example in a case of not performing the preferential display processing of the accompanying information according to an embodiment of the present invention.

11A to 11D and FIG. 12. In FIG. 12, comments 1101, 1104 are shown by double-shaded dots or as white-blank areas, a marker 1102 is shown by a black circle, a marker 1103 hidden by other display objects is shown by a broken-line circle and a display object 1105 is shown by surrounding it by a thick line. In FIG. 12, all of the comments 1101 and 1104 are displayed on the front-most face with the same size. Here, the examples that the display method has been changed supposing that the priority is lowered in order of 1101a, 1101b and 1104 in regard to the priority of the comments are shown in FIGS. 11A to 11D. FIG. 11A is a case where the size that the comment is displayed is varied in accordance the priority, and the comment that is higher in priority is displayed larger. As for the comment to be displayed small, the display content is adjusted by a method of reducing the number of characters to be displayed or reducing the size of the character. FIG. 11B is a case where the depth that the comment is to be displayed has been varied in accordance with the priority, only the comment 1101a that is the highest in priority is set onto the front-most face and the others 1101b and 1104 are displayed behind the display object 1105. FIG. 11C is a case where the color and the transparency of the comment have been varied in accordance with the priority, and FIG. 11D shows a case where only the comment 1101a that is the highest in priority has been displayed. Incidentally, in regard to the comment that is low in priority, it is possible to change the display state by a selecting operation such as mouse click and so forth of the user.

In addition, in a case where the positions of the accompanying information such as the marker, the ROI and so forth are relevant to specific coordinates of the 3D data (S314), the drawing control unit 7 sets the positions corresponding to the specific coordinates of the 3D data (S316). Further, in a case where they are relevant to other pieces of accompanying information such as the comments and so forth given to the marker and the ROI (S318), the drawing control unit 7 adds the lead line between the accompanying information and the accompanying information to be an object thereof to indicate the relevance and sets a position in the vicinity of the object in the arrangeable area (S320).

In the foregoing procedure, arrangement of the accompanying information is performed within the range of the stereoscopically visible depth.

REFERENCE SIGNS LIST

1: medical image display device, 3: display unit, 5: control unit, 6: list management unit, 7: drawing control unit, 8: drawing processing unit, 10: storage unit, 15: medical information management server, 18: storage unit, 20: network, 21: medical image imaging device, 22: in-hospital information system, 30: drawing setting, 31: drawing method, 32: drawing parameter, 33: range of values to be objects, 35: drawing element, 36: drawing object, 37: 3D data name, 38: mask name, 40: information on display unit, 41: information on output image required for stereoscopic vision, 42: image format, 43: number of images, 44: image generation condition, 45: recommended range of stereoscopically visible depth position, 46: range of character information, 47: range of graphic information, 50: screen, 51: stereoscopic image display area, 52: section pattern display area, 53: tool area, 54: medical image, 56: ROI (2D), 57: ROI (3D), 58: comment, 59: measurement tool, 60: mouse cursor, 70: X-axis, 71: Y-axis, 72: Z-axis, 80: display/arrangement plan of accompanying information, 81: fixing/unfixing of depth position, 82: fixing/unfixing of intra-screen position, 83: switching propriety of display/non-display, 84: display priority, 85: relevance to specific coordinates of original data or another piece of accompanying information, 86: relevance to user operation, 87: occulusion processing with 3D data, 91: valid 3D data area, 92: area free from occurrence of occulusion with valid 3D data area, 93: area not overlapping valid 3D data area and not coming behind valid 3D data area by occlusion.

The invention claimed is:

1. An image display device, comprising:
a display unit that displays an output image that has been drawn;
a storage unit that has stored an array of 3D signal values that is a drawing object, mask information for designating an object area for drawing in the array of the 3D signal values, information for designating a drawing method for a 2D image based on the array of the 3D signal values, accompanying information that has been related to the drawing object, information on arrangement and display plans that has been set for the accompanying information, and information relevant to characteristics of the display unit, wherein the information on the arrangement plans includes fixing or unfixing of a depth position on an axis that is vertical to a screen of the display unit, fixing or unfixing of an intra-screen position of the display unit, and presence/absence of relevance to a specific coordinate position included in the drawing object to which the accompanying information has been related, and the information on the display plans includes a display priority of the accompanying information;
a drawing control unit that computes the position of the accompanying information in a coordinate system of the 3D signal value that is to be the drawing object on the basis of the mask information, the information for designating the drawing method for the 2D image, the information on the arrangement and display plans and the information relevant to the characteristics of the display unit and stores it into the storage unit; and
a drawing processing unit that generates an output image to be displayed on the display unit by integrating together a 3D data area to be drawn on the basis of the information for designating the drawing method for the 2D image for the area that has been designated by the mask information in the array of 3D signal values that is the drawing object, and an accompanying information area to be drawn on the basis of information on the position of the accompanying information that has been determined by the drawing control unit for the accompanying information.

2. The image display device according to claim 1, wherein the display unit has a function of performing stereoscopic display, and the information relevant to the characteristics of the display unit included in the storage unit includes a format, an amount and an image generation condition of an image to be required for performing the stereoscopic display by the display unit, information relevant to a range of a depth position when performing the stereoscopic vision on the display unit, and information relevant to a specific depth position.

3. The image display device according to claim 1, wherein the drawing control unit computes the position of the accompanying information on the basis of the information relevant to the characteristics of the display unit, and the information on the arrangement and display plans.

4. The image display device according to claim 1, wherein the drawing processing unit generates the output image based on a case of occurrence of overlapping or occulusion of areas in the 3D data area and an accompanying information area.

5. The image display device according to claim 4, wherein, in computation of the position of the accompanying information by the drawing control unit, in the information on arrangement and display plans set for the accompanying information, within a range of a depth position designated in the information relevant to the characteristics of the display unit, for the accompanying information set such that the depth position on the axis vertical to the screen of the display unit is unfixed and the intra-screen position of the display unit is fixed, in a case where the specific depth position is defined in the information relevant to the characteristics of the display unit within a range on the front side ahead of a volume data area, a depth position that is the nearest to the depth position is set, and in a case where the specific depth position is not defined, a depth position on the front side that is the nearest to the volume data area is set.

6. The image display device according to claim 4, wherein, in computation of the position of the accompanying information by the drawing control unit, in the information on arrangement and display plans set for the accompanying information, setting of the position is performed by the drawing control unit, after having indicated the relevance to the specific coordinate position or another piece of accompanying information by adding accompanying information including a lead line to accompanying information set such that the depth position on the axis vertical to the screen of the display unit is unfixed, and the intra-screen position of the display unit is unfixed, and there exists the relevance to the specific coordinate position included in the drawing object to which the accompanying information has been related or another piece of accompanying information.

7. The image display device according to claim 1, wherein the drawing control unit, in a case where there exists accompanying information that information on the priority relevant to the accompanying information is set such that a displaceable area is included in drawing processing, if any, computes at least one of an area that does not overlap the 3D data area and an area that occulusion with the 3D data area does not occur in a case where the accompanying information has been arranged, on a specific depth position, from a depth image that has been drawn by using the 3D data area to set it as an accompanying information arrangeable area, and determines propriety of display and arrangement of the accompanying information on the basis of a shape of the accompanying information arrangeable area.

8. The image display device according to claim 1, wherein the drawing control unit, in a case where there exist a plurality of pieces of accompanying information that information on the priority relevant to the accompanying information is set such that preferential display is performed in accordance with priority order, saves the information for designating the drawing method for the 2D image when the accompanying information has been given by relating it to the accompanying information, and the control unit preferentially displays the accompanying information in accordance with the similarity between a drawing method for the 2D image based on the array of the 3D signal values saved by being related to the accompanying information and a drawing method for the 2D image based on the array of the 3D signal values that are being currently displayed.

9. The image display device according to claim 1, wherein processing in a case of occurrence of overlapping or occulusion of areas in the 3D data area and the accompanying information area, in a case where the 3D data area is present on the front side ahead of the accompanying information area, selects whether an output image is to be generated by using pixels of a 2D image that the depth displayed by each depth image in relation to each pixel of the 2D image is present on the front side, or whether the output image is to be generated by using the pixel of the 2D image generated from the accompanying information without referring to the depth image in relation to the area of the accompanying information, and in a case where there exists accompanying information for preferring display of the accompanying information, in the drawing processing unit, a preferential display image that indicates whether each pixel is a preferential display area with two values is generated in addition to the 2D image and the depth image from the accompanying information area, and integration of the output images is performed.

10. An image display method executed by an image display device including a storage unit, a drawing control unit, a drawing processing unit and a display unit, the method comprising:
   storing, by the storage unit, an array of 3D signal values that is a drawing object, mask information for designating an object area for drawing in the array of the 3D signal values, information for designating a drawing method for a 2D image based on the array of the 3D signal values, accompanying information that has been related to the drawing object, information on arrangement and display plans that has been set for the accompanying information, and information relevant to characteristics of the display unit, wherein the information on the arrangement plans includes fixing or unfixing of a depth position on an axis that is vertical to a screen of the display unit, fixing or unfixing of an intra-screen position of the display unit, and presence/absence of relevance to a specific coordinate position included in the drawing object to which the accompanying information has been related, and the information on the display plans includes a display priority of the accompanying information,
   computing, by the drawing control unit, the position of the accompanying information in a coordinate system of the 3D signal value that is to be the drawing object on the basis of the mask information, the information for designating the drawing method for the 2D image, the information on the arrangement and display plans and the information relevant to the characteristics of the display unit, and storing it into the storage unit,
   generating, by the drawing processing unit, an output image to be displayed on the display unit by integrating together a 3D data area to be drawn on the basis of the information for designating the drawing method for the 2D image for the area that has been designated by the mask information in the array of 3D signal values that is the drawing object, and an accompanying information area to be drawn on the basis of information on the position of the accompanying information that has been determined by the drawing control unit for the accompanying information, and displaying, by the display unit, the drawn output image.

* * * * *